United States Patent [19]
Reid et al.

[11] Patent Number: 5,637,694
[45] Date of Patent: Jun. 10, 1997

[54] PREPARATION AND USE OF 7-[(2-CARBOALKOXY-1-METHYLETHENYL)AMINO]-3-HYDROXYMETHYL-3-CEPHEM-4-CARBOXYLIC ACIDS

[75] Inventors: J. Gregory Reid, Manlius; Paul R. Brodfuehrer; Patrick R. Smith, both of Syracuse, all of N.Y.

[73] Assignee: Briston-Myers Squibb Company, Princeton, N.Y.

[21] Appl. No.: 628,426

[22] Filed: Apr. 5, 1996

Related U.S. Application Data

[62] Division of Ser. No. 438,322, May 10, 1995, Pat. No. 5,552,542.
[51] Int. Cl.$^6$ .................................................. E07D 501/28
[52] U.S. Cl. .................................................. 540/230
[58] Field of Search ................................................ 540/230

[56] References Cited

U.S. PATENT DOCUMENTS

| | | | |
|---|---|---|---|
| 4,245,088 | 1/1981 | Tsushima et al. | 544/16 |
| 4,584,371 | 4/1986 | Timko | 544/16 |
| 4,908,444 | 3/1990 | Naito et al. | 540/230 |
| 5,221,739 | 6/1993 | Wildfeuer | 540/230 |

FOREIGN PATENT DOCUMENTS

| | | |
|---|---|---|
| 53-025589 | 3/1978 | Japan. |
| 57-058690 | 4/1982 | Japan. |

OTHER PUBLICATIONS

Peter H. Bentley, Gerald Brooks and Iskander I. Zomaya, "Phthalidyl Esters of Cephalosporins", *Terahedron Letters*, No. 41, pp. 3739–3742, 1976.

Elisabeth Dane and Toni Dockner, "β–Dicarbonylverbindungen als Aminoschutzgruppen bei Peptidsynthesen, (III.)", *Chemische Berichte*, 98, pp. 789–796, 1965.

Theodora W. Greene and Peter G.M. Wuts, "Protective Groups in Organic Synthesis", *John Wiley & Sons, Inc.*, Second Edition, pp. 309–315, 372, 1991.

Nobuharu Kakeya, et al, "KY–109, A New Bifunctional Pro–drug of a Cephalosporin", *The Journal of Antibiotics*, vol. 38, No. 3, pp. 380–389, Mar. 1985.

Earle Van Heyningen, "The Chemistry of Cephalosporin Antibiotics. III. Acylation of Cephalosporadesates", *J. Med. Chem.*, vol. 8, pp. 22–25, 1965.

*Primary Examiner*—John M. Ford
*Attorney, Agent, or Firm*—David M. Morse

[57] ABSTRACT

This invention relates to a method of producing 3-alkanoyloxymethyl-3-cephem-4-carboxylic acids from 3-hydroxymethyl-3-cephem-4-carboxylic acids in an aqueous medium for a practical, large-scale production. Moreover, the invention provides an ideal intermediate for the process.

3 Claims, No Drawings

PREPARATION AND USE OF 7-[(2-CARBOALKOXY-1-METHYLETHENYL) AMINO]-3-HYDROXYMETHYL-3-CEPHEM-4-CARBOXYLIC ACIDS

CROSS-REFERENCE TO RELATED APPLICATION

This is a division of application U.S. Ser. No. 08/438,322, filed May 10, 1995, now U.S. Pat. No. 5,552,542.

BACKGROUND OF THE INVENTION

The antibacterial compound cephalosporin C was first isolated by Newton and Abraham (*Nature*, 175:548, 1955). Cephalosporin C is produced by fermentation, generally by the organism cephalosporium acremonium.

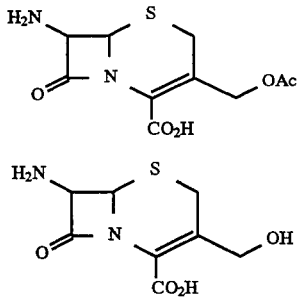

7-Aminocephalosporanic acid (7-ACA), 1, is an important intermediate in the synthesis of many cephalosporin antibiotics. It is generally obtained from cephalosporin C following chemical cleavage of the acyl group attached to the 7-amino substituent.

Deacetyl cephalosporin C is a major by-product in the fermentation and is converted to deacetyl 7-ACA, 2, in the process of converting cephalosporin C to 7-ACA. The problem associated with the formation of these side products on the yield of 7-ACA, and a possible solution to this problem is offered in U.S. Pat. No. 5,221,739 and U.S. Pat. No. 4,908,444. More specifically, they teach the direct reacylation of 3-hydroxymethyl-3-cephem-4-carboxylic acids in an aqueous medium.

SUMMARY OF THE INVENTION

This invention relates to a method of producing 7-aminocephalosporanic acid from deacetyl 7-ACA in an aqueous medium for practical, large-scale production. Moreover, the invention provides an ideal intermediate for the process.

DETAILED DESCRIPTION OF THE INVENTION

The selective acylation of hydroxy group in the presence of free amino group generally requires a protection of the amino group. The choice of protecting group varies with each application, but in general the requirements are that the protecting group attaches readily and in high yield, that it prevents the undesired reaction from occurring with the amino group, and that it can be removed readily and in high yield. In many cases compromises must be struck among these considerations when choosing the best protecting group.

The most common protecting groups for amines are alkoxycarbonyl groups, or carbamates. Two in particular, carbobenzyloxy (CBZ) and t-butoxycarbonyl (BOC) are very often employed. Less common protecting groups are acyl groups (to form an amide), alkylidene groups (to form an imine or Schiff base), hydronium ions (to form a salt), sulfonyl groups (to form a sulfonamide), or in some cases a silyl group (to form a silazide) or a triphenylmethyl group (to form a triphenylmethyl amine). In general, these less common protecting groups can be readily attached, but often lack adequate protecting ability and ease of removal. Generally speaking, those that are very good at preventing unwanted reactions of the amine are often difficult to remove, and those that are readily removed do not always provide adequate protection.

In exploring for an ideal protecting group for the amino group of compound 2, we found that protecting the amine as an enamine offered both advantages of ready attachment and removal, and was also suitable for large scale production. The reaction of 2 with alkyl esters of acetoacetic acid gave in high yield the previously unknown enamines of formula 3, and that compounds of formula 3 could be selectively reacted with acetic anhydride to give compounds of formula 4, which could then be subsequently converted to 7-ACA by acidic hydrolysis. Enamines have been used occasionally for the N-protection of amino acids and 7-amino groups of cephlosporins in the past, see for example, P. H. Bentley et al., *Tetrahedron Letters*, No. 41, pp 3739–3741 (1976), but their ability to be used in the present context was quite surprising, particularly, since, Isamu et al, in Japan Kokai 78 25,589 (Chemical Abstract, Vol 89: 109529t), teach that acylation with acyl chloride of a cephalosporin with the 7-amino group derivatized to an enamine leads to the N-acylated product, suggesting that enamine would not prevent acylation at nitrogen.

The process of this invention can be illustrated with the following Scheme. In the Scheme, the bonds represented by ~ in compounds 3 and 4 indicate either the E and Z isomer. R is $C_{1-6}$ alkyl, preferably methyl or ethyl.

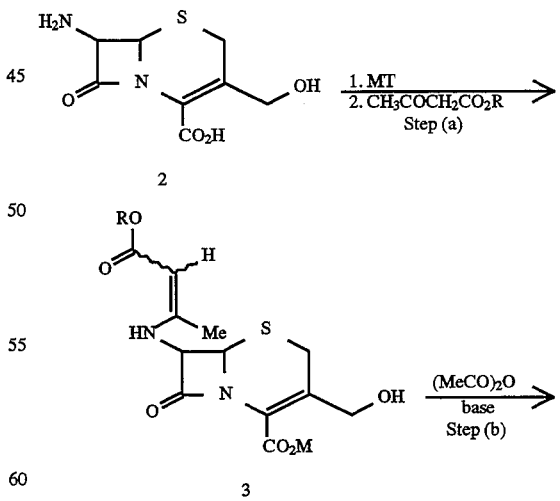

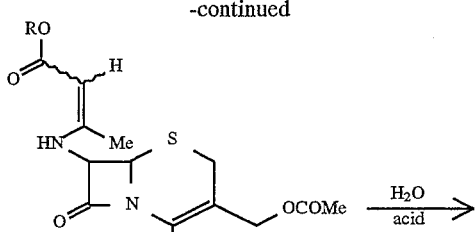

-continued

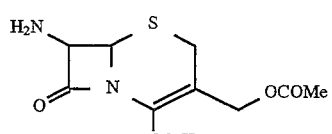

Step (a): A base or a mixture of bases is needed for Step (a). Base can be any inorganic or organic base with pKa's between 4 to 14. Organic base refers to tri$C_{1-6}$alkylamine, pyridine, dimethylaminopyridine, etc. MT refers to a preferred base, in which M is alkali or alkaline earth metal, preferably sodium or potassium; and T includes hydroxide, acetate, carbonate, bicarbonate and phosphate. Thus, examples of MT are hydroxide, acetate, carbonate, bicarbonate, phosphate of alkali or alkaline earth metals. Even more preferred base is sodium or potassium hydroxide, or sodium or potassium acetate. Step (a) works best with a large excess of alkyl acetoacetate, so it is convenient to use this reagent as solvent, with or without other organic co-solvents. Preferably the reaction is run under anhydrous condition. The possible temperature range of Step (a) is between 0° to 55° C. Naturally the preferred temperature will depend on the choice of base and solvent.

Step (b): The solvent system which can be employed for Step (b) is water alone or mixtures of water and organic solvent. Some water is required for solubility of the substrate and base that is to be employed, but water also competes with the substrate for acetic anhydride, so it should be minimized. Preferred solvent system is 50% acetone in water. A base, or a mixture of bases is required for Step (b). Both inorganic and organic base can be used. However, inorganic bases are preferred to organic bases, because higher levels of undesired by-product (lactone) are seen with tertiary amine bases. Common base that can be employed includes alkali or alkaline earth hydroxide, dimethylaminopyridine, etc. The reaction pH must be maintained at 7–11, preferably between 9–10. The preferred temperature range is in the range of –10° to 40° C., and even more preferably between 0° to 5° C.

Step (c): Final pH of the reaction mixture should be adjusted to 3–4 by addition of acid. A wide variety of acid can be used for Step (c); it can be mineral acid, such as hydrogen chloride, hydrogen bromide, hydrogen iodide; or p-toluenesulfonic acid, etc. Preferred final pH is 3.5. While adjusting the pH and isolating the product, the temperature is preferably maintained between –10° to 40° C., and even more preferably 0° to 5° C.

As used herein, $C_{1-6}$ alkyl means a straight or branched saturated carbon chain having from one to six carbon atoms; examples include methyl, ethyl, n-propyl, isopropyl, n-butyl, t-butyl, sec-butyl, isobutyl, n-pentyl, sec-pentyl, isopentyl, and n-hexyl. Alkali metal refers to a metal in Group IA of the periodic table, preferably lithium, sodium and potassium. Alkaline earth metal refers to a metal in Group IIA of the periodic table, preferably calcium and magnesium.

The specific examples that follow illustrate the instant invention, and are not to be construed as limiting the invention. The methods may be adapted to variations in order to produce the compounds embraced by this invention, and without departing from the spirit of the invention. Further, variations of the methods to produce the same compounds in somewhat different manner will also be evident to one skilled in the art.

Example 1. Preparation of 7-[2-carbomethoxy-1-methylethylene)amino]-3-hydroxymethyl-3-cephem-4-carboxylic acid potassium salt from desacetyl 7-amino cephalosporanic acid.

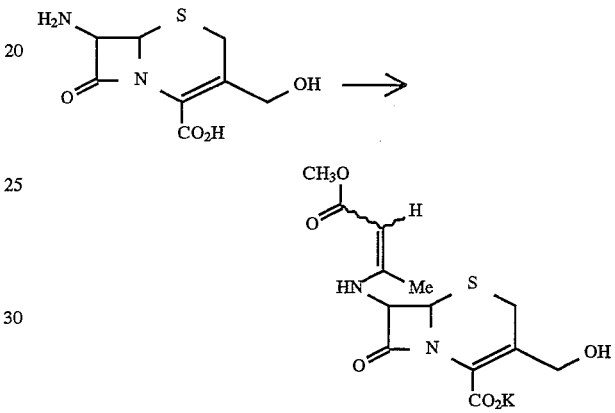

In a 500 ml three-neck round bottom flask, desacetyl-7-amino cephalosporanic acid (20.0 g, 0.0837 mole) was suspended in methanol (140 ml) with vigorous overhead stirring at 0°–5° C. A solution of KOH (5.36 g, 0.0830 mole) in methanol (60 ml) was then added slowly over ca. 1 h and the reaction mixture stirred at 0°–5° C. for 30 min. The resulting thin suspension was then added in a steady stream to methyl acetoacetate (100 ml) over ca. 2–3 min at 0°–5° C. The resulting mixture was then stirred at 0° C. for 3.5–4 h. The methanol was then removed in vacuo and the resulting wet residue stirred in ethyl acetate (100 ml) at 0°–5° C. for 1 h. The solid is then collected via vacuum filtration and the cake washed with ethyl acetate (2×20 ml). The cake is then dried in vacuo at 40° C. to yield ca. 25.48 g (80.1%) of 7-[2-carbomethoxy-1-methylethylene)amino]-3-hydroxymethyl-3-cephem-4-carboxylic acid potassium salt.

Example 2. Preparation of 7-amino cephalosporanic acid from 7-[(2-carbomethoxy-1-methylethylene)amino]-3-hydroxymethyl-3-cephem-4-carboxylic acid potassium salt.

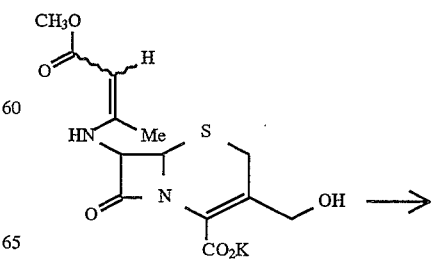

-continued

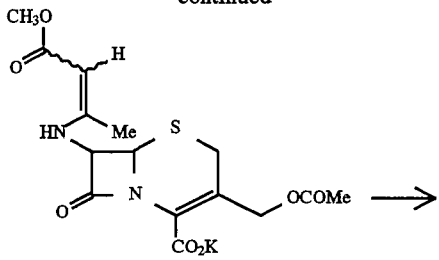

→

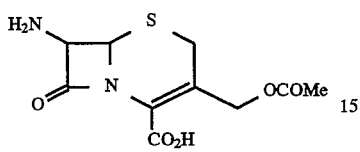

7-[2-Carbomethoxy-1-methylethylene)amino]-3-hydroxymethyl-3-cephem-4-carboxylic acid potassium salt (10.00 g, 0.0273 mol) was dissolved in acetone (25 ml) and water (25 ml) with stirring at 0°–5° C. and dimethylaminopyridine (33 mg. 0.27 mmol) added at pH 9–10. Acetic anhydride (6.44 ml, 0.0682 mol) was then added dropwise over ca. 15 min while maintaining pH at 9–10 by periodic addition of 20% KOH. The reaction was stirred under these conditions for 30 min and ethyl acetate (10 ml) added. The pH was lowered to 3.5 via addition of 6N HCl at 0°–5° C. and the resulting slurry stirred for 1 h. The solid was then collected via vacuum filtration and washed with acetone (15 ml). The cake was then dried at 40° C. in vacuo to yield ca. 7.00 g (94.2%) of 7-amino cephalosporanic acid.

We claim:

1. A compound of the formula

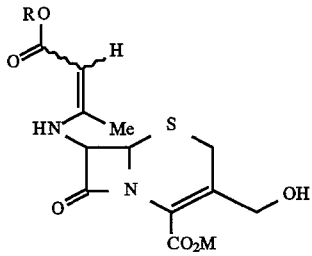

in which M is a metal selected from Group Ia or IIa of the periodic table, and R is $C_{1-6}$ alkyl.

2. A compound of claim I in which R is methyl or ethyl, and M is potassium or sodium.

3. A compound of claim 2 in which R is methyl, and M is potassium.

* * * * *